United States Patent
Souppe

(10) Patent No.: US 7,247,331 B2
(45) Date of Patent: Jul. 24, 2007

(54) MILK PROTEIN ISOLATE AND METHOD FOR PREPARING SAME

(75) Inventor: Jérôme Souppe, Rennes (FR)

(73) Assignee: Compagnie Laitiere Europeenne (FR)

( * ) Notice: Subject to any disclaimer, the term of this patent is extended or adjusted under 35 U.S.C. 154(b) by 0 days.

(21) Appl. No.: 10/519,131

(22) PCT Filed: Jun. 30, 2003

(86) PCT No.: PCT/FR03/02015

§ 371 (c)(1),
(2), (4) Date: Aug. 4, 2005

(87) PCT Pub. No.: WO2004/004482

PCT Pub. Date: Jan. 15, 2004

(65) Prior Publication Data

US 2006/0040025 A1     Feb. 23, 2006

(30) Foreign Application Priority Data

Jul. 2, 2002   (FR) ................... 02 08234

(51) Int. Cl.
*A23C 1/00*      (2006.01)
*A23J 1/20*      (2006.01)
*A23L 2/38*      (2006.01)
*A61K 47/00*     (2006.01)
*C07K 1/18*      (2006.01)

(52) U.S. Cl. .............. 426/491; 426/271; 426/580; 426/587; 426/588; 426/590; 514/775; 530/416

(58) Field of Classification Search ......... 426/491, 426/580–590; 424/94.1, 535; 514/775; 530/416
See application file for complete search history.

(56) References Cited

U.S. PATENT DOCUMENTS

| | | | |
|---|---|---|---|
| 5,149,647 A | 9/1992 | Burling | |
| 5,976,597 A | 11/1999 | Takada et al. | |
| 6,010,698 A | 1/2000 | Kussendrager et al. | |
| 6,096,870 A | 8/2000 | Miranda et al. | |
| 6,319,522 B1 | 11/2001 | Ballard et al. | |

FOREIGN PATENT DOCUMENTS

| | | | |
|---|---|---|---|
| EP | 0704218 A | 4/1996 | |
| EP | 1010430 A | 6/2000 | |
| FR | 2 443 867 A | 7/1980 | |
| JP | 08165249 | 6/1996 | |
| JP | 09187250 A | 7/1997 | |
| JP | 11089946 | 10/2000 | |
| WO | WO 93/13676 A | 7/1993 | |
| WO | WO 97/27757 A | 8/1997 | |
| WO | WO 99/15024 A | 4/1999 | |

OTHER PUBLICATIONS

Takadaet al., "Whey protein stimulates the proliferation and differentiation of osteoblastic MC3T3-E1 cells", Biochemical and Biophysical Research Communications, vol. 223, 1996, pp. 445-449.

Hashimoto et al "Epithelial properties of human intestinal Caco-2 cells cultured in a serum-free medium" Cytotechnology, Springer, Netherlands, vol. 13(3) Oct. 1993 175-184.

Haak-Frendscho et al., "Transforming growth factor-β1 inhibits activation of macrophage cell line RAW 264.7 for cell killing." Clinical & Experimental Immunology, 1990 clin. exp. Immunol. 82: 404-410.

Yamamura et al "High Mobility Group-like Protein in Bovine Milk Stimulates the Proliferation of Osteoblastic MC3T3-E1 Cells" Biochemical & Biophysical Research Communications, vol. 261, 1999, pp. 113-117.

Toba et al "Milk basic protein: a novel protective function of milk against osteoporosis" Bone, Elsevier Inc, California, USA, vol. 27(3), Sep. 2000, pp. 403-408.

Rogers et al "Transforming growth factor beta in bovine milk: concentration, stability and molecular mass forms" Journal of Endocrinology, 1996 J. of Endocrinology 151: 77-86.

Hahn et al., "Bovine whey fractionation based on cation-exchange chromatography", *Journal of Chromatography A. Elsier Science*, vol. 795, No. 2, Feb. 6, 1998, pp. 277-287.

Chiu et al., "Fractionation of lactoperoxidase and lactoferrin from bovine whey using a catiaon exchange membrane", *Journal of Food Science 1997 Dep. Of Food Sci.*, Univ. of Wisconsin, vol. 62, No. 5, pp. 996-1000.

*Primary Examiner*—Maryam Monshipouri
*Assistant Examiner*—Marsha Tsay
(74) *Attorney, Agent, or Firm*—Alston & Bird LLP

(57) ABSTRACT

The invention concerns a method for isolating milk proteins from milk or from whey comprising steps which consist in passing the milk or whey over a cation-ex-changing resin, eluting the fraction retained by an aqueous salted solution and desalting and sterilizing the eluate. The invention also concerns a milk protein fraction obtained by said method and its use for preparing pharmaceutical and food compositions.

Figure 1:
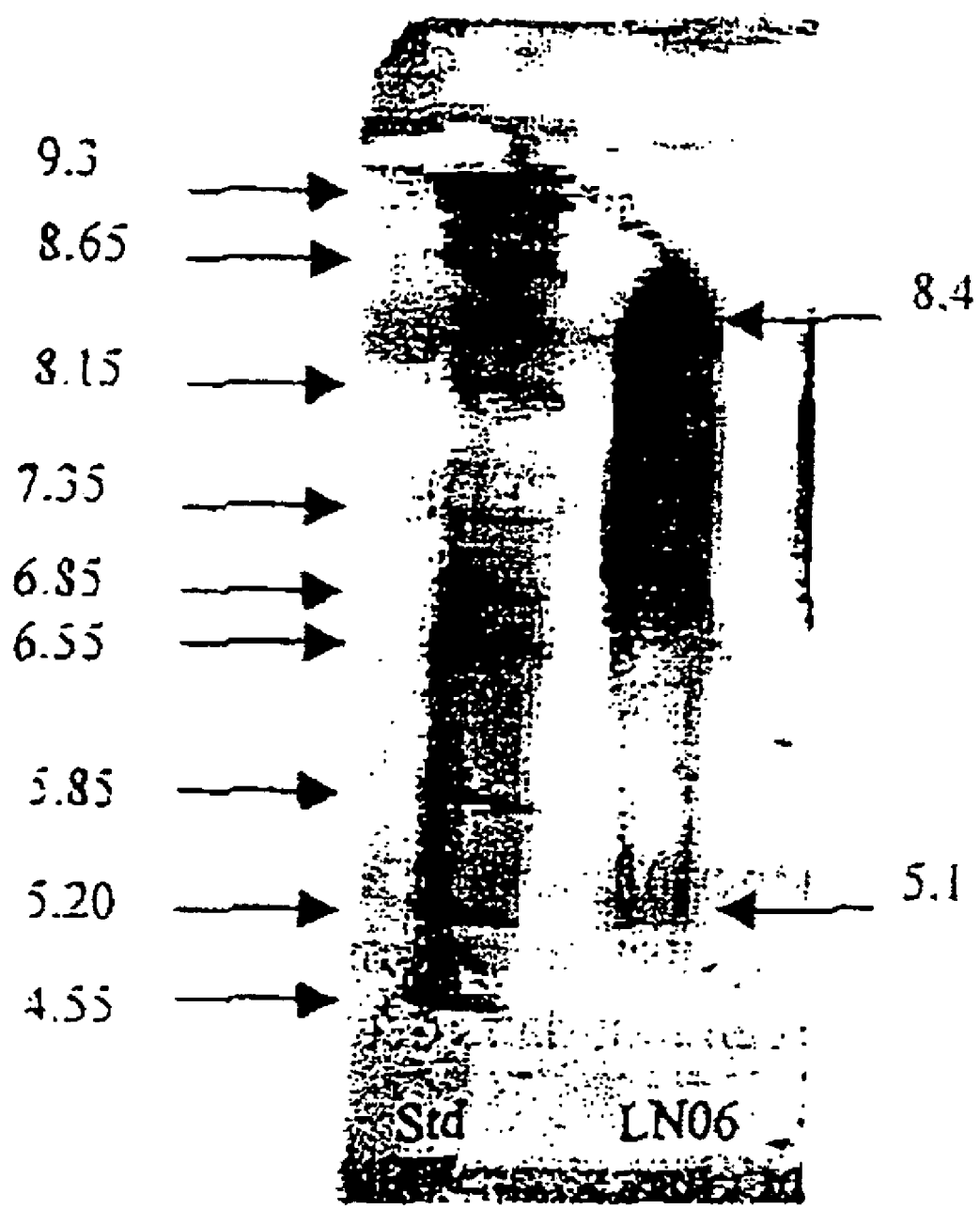

33 Claims, 1 Drawing Sheet

MILK PROTEIN ISOLATE AND METHOD FOR PREPARING SAME

CROSS REFERENCE TO RELATED APPLICATIONS

This application is a national stage application filed under 35 USC 371 of International Application No. PCT/FR03/0201 5, filed Jun. 30, 2003, which claims priority from French patent application 02 08234 filed Jul. 2, 2002.

FIELD AND BACKGROUND OF THE INVENTION

The subject of the present invention is a novel process for isolating milk proteins, the composition, milk protein isolate or milk protein fraction, resulting therefrom and its applications, in particular its food and pharmaceutical applications.

Several prior art documents describing the purification of milk proteins are known.

The document EP-253395 describes the production of a bovine lactoferrin of high purity (>80% in a single step or >98% in two steps) by adsorption of milk or of whey onto a cation-exchange resin comprising carboxymethyl radicals, followed by rinsing and desorption of the lactoferrin.

The document EP-348508 also describes a process for preparing a bovine lactoferrin of high purity (>95%) by adsorption of milk or whey onto a cation-exchange resin of the polysaccharide type comprising sulfuric acid ester functional groups and elution with an aqueous salt solution.

The document EP-298875 describes a process which makes it possible to isolate certain whey proteins by adsorption onto a porous mineral support in the form of grains, these grains being coated with an amine-containing polysaccharide layer having at the surface acid functional groups such as carboxylic or sulfonic groups.

The document EP-418704 describes a process for sequentially purifying lactoferrin and lactoperoxidase by elution on a column loaded with a polysaccharide resin grafted by sulfonic acid groups.

The document U.S. Pat. No. 6,096,870 describes a process for the sequential separation of whey proteins by elution on cationic resins.

The document EP-1017286 describes a process for the sequential separation of whey proteins by radial flow chromatography.

Lactoferrin and lactoperoxidase are milk proteins with advantageous properties, their capacity to bind iron confers on them a role of antibacterial agent against bacteria whose metabolism requires large quantities of iron. Lactoperoxidase is essential for labeling protein with iodine. Lactoferrin promotes the growth of lymphocytes and promotes the absorption of iron by the body; it regulates the differentiation of leukocytes and it inhibits the peroxidation of lipids.

However, all these documents relate to processes aimed at a lactoferrin and/or a lactoperoxidase which are as pure as possible, that is to say processes aimed at reducing as much as possible the proportion of the other proteins initially present in milk or whey. In addition, the conditions for binding the raw material and for eluting the proteins are gentle conditions, with slow flow of materials. On the other hand, the objective which the applicant set itself is the production of a milk protein fraction comprising, among other constituents, lactoferrin and lactoperoxidase, but comprising especially a higher proportion of the other proteins than in the starting milk or whey. For that, the applicant has developed a process with much higher flows than those described in the documents analyzed above, this process allowing a more selective binding in relation to certain proteins.

The document WO93/13676 discloses a process which makes it possible to isolate lactoferrin and lactoperoxidase from whey by passage over a cation-exchange resin at high flow. This process is distinguishable from the process according to the present invention in that the flow is greater than in the process according to the invention (greater than 5 m/h) and in that it aims to purify the lactoferrin and the lactoperoxidase, and not to obtain a particular milk protein fraction containing a relatively high level of the other proteins and endowed with improved biological properties.

There is also known, from the document EP-704218, an agent intended for strengthening the bones, this agent comprising a basic protein fraction or a basic peptide fraction, derived from milk and obtained by passing milk over a cationic resin and eluting. However, the adsorption and elution conditions described in this document are distinct from those used in the process according to the invention and make it possible to isolate a protein fraction distinct from that obtained according to the present invention.

The documents JP-8165249, JP-9187250, JP-9294537 and EP-1010430 describe compositions intended for strengthening the bones and/or for preventing periodontal diseases, these compositions comprising a milk-derived basic protein fraction obtained by adsorption of the milk and elution on a cationic resin. However, the adsorption and elution conditions described in these documents are distinct from those used in the process according to the invention and make it possible to isolate a protein fraction distinct from that obtained according to the present invention.

Thus, it is surprising that the applicant has discovered a novel process for isolating milk proteins which make it possible to obtain a milk protein fraction endowed with improved biological properties, in particular a milk protein fraction promoting growth of the osteoblasts and inhibition of the proliferation of the preosteoclasts and of the osteoclasts.

SUMMARY OF THE INVENTION

The subject of the invention is a process for isolating milk proteins from milk or whey comprising the following steps:
a) the milk or the whey is sterilized and defatted;
b) the milk fraction derived from step a) is passed over a cation-exchange resin conditioned in an elution column;
c) the fraction retained on the resin is eluted with an aqueous salt solution;
d) the eluate resulting from step c) is desalted, preferably by ultrafiltration and diafiltration, and then sterilized, preferably by microfiltration.

This process being characterized in that:
α) the cation-exchange resin is a resin grafted onto strong acid functional groups;
the parameter BV denoting the ratio of the volume of raw material to the volume of wet resin in the column,
the parameter SV denoting the ratio of the rate of feeding the column to the volume of wet resin in the column,
the parameter LV denoting the ratio of the rate of feeding the column to the section of the column,
β) during step b), the binding parameters have the following values:
$BV_f$ is between 50 and 400, preferably between 80 and 300;

$SV_f$ is between 2 and 40 h$^{-1}$;

$LV_f$ is greater than or equal to 1 m/h and less than or equal to 5 m/h.

γ) during step c), the elution parameters have the following values:

$BV_e$ is between 1.5 and 7;

$LV_e$ is less than 1 m/h, preferably less than 0.5 m/h.

It is possible to use as starting material in the process according to the invention either milk or whey, preferably derived from cows. Whey is the residual liquid obtained after extracting the proteins and the fat from milk or milk serum. Three categories of whey can be distinguished. The first two categories are classified according to the acidity of the whey which may be less than or greater than 1.8 g of lactic acid/l: sweet whey, derived from the manufacture of cooked or uncooked pressed cheese (emmenthal, saint-paulin, etc.) and acid whey, derived from casein or other cheeses obtained by mixed or lactic curdling (soft cheeses, fromage frais). The average composition of sweet whey is, as a guide, for 61 g of dry matter content per kg of whey, from 42 to 48 g of lactose, 8 g of proteins, 2 g of fat, 5 to 7 g of minerals, 1 to 5 g of lactic acid and the remainder as minerals and vitamins.

The ideal whey obtained by microfiltration of milk on a support having an average porosity of 0.1 μm is known.

According to a first variant of the invention, there is used as starting material milk, and advantageously cows' milk, whose composition allows, by the process according to the invention, the production of a protein isolate having more advantageous biological properties. This variant also makes it possible to obtain a protein yield greater than the variants using whey as starting material.

According to a second preferred variant of the invention, acid whey from casein manufacture is used as starting material. This variant represents an important economic advantage since the starting material is a by-product derived from industrial exploitation and therefore of a low cost.

In the first step of the process, the milk or whey is sterilized and defatted by skimming, in a known manner:

The skimming of milk denotes the separation of the cream from the milk, regardless of the process used to obtain this separation.

Traditionally, the manufacture of cream is carried out according to a natural process: when the milk is allowed to stand, the elements constituting it separate according to their density. The fat globules, being lighter than water, rise to the surface to form a layer of cream. In industrial production, the formation of the cream is accelerated by passing the milk into a centrifugal cream separator.

Usually, the pasteurization is carried out by controlled heating of short duration so as to remove the pathogenic microorganisms which may be present in the cream. Advantageously, the pasteurization is carried out at a temperature of between 65 and 95° C., preferably between 80 and 95° C. It may be possible for example to treat the milk or the whey for 15 seconds at a temperature of between 65 and 82° C. It is also possible to sterilize the starting milk or whey by microfiltration on a filter having pores with a diameter ranging from 0.1 to 2 μm.

The sterile and defatted raw material is then passed over a cation exchange resin. According to the invention, the cation-exchange resin is a resin grafted by strong acid functional groups and having an ion-exchange capacity of between 200 and 1000 μE/ml, preferably between 400 and 700 μE/ml. The expression strong acid functional group is understood to mean an acid functional group having a pKa≦2. In particular, it may be grafted by sulfonic acid functional groups, generally in the form of sulfonate salts for their use, the nature of the salt determined by the solution which served to pack the column before carrying out the process. Preferably, grafting by aromatic or aliphatic groups carrying sulfonic acid functional groups, still more preferably in the form of propyl sulfonate salts, is chosen. The resin on which the sulfonic acid functional groups are grafted may be of any type, in particular of the polyacrylic or polystyrene type. The particle size of the resin is advantageously between 100 μm and 900 μm, preferably between 200 and 750 μm, still more preferably between 250 and 600 μm. The resin which can be used according to the invention should preferably have a density greater than 1.15.

Among the commercially available resins which can be used in the present invention, there may be mentioned in particular: the Trisacryl SP® resin marketed by the company BIOSEPRA, the MacroPrep High S® resin marketed by the company BioRad. Preferably, a polystyrene resin grafted by alkyl or aryl sulfonate functional groups is chosen.

The resin is conditioned in a column before its use, in a manner known to the person skilled in the art, by treating with a disinfectant solution and rinsing in order to avoid contamination by microorganisms. It is then optionally equilibrated by passing a buffer solution and rinsing.

Step b) of binding the sterile and defatted raw material, milk or whey, is carried out under the following preferential conditions:

The resin is conditioned in a column whose temperature is kept between 2 and 15° C., preferably between 4 and 12° C. Preferably the column is fed with raw material through the bottom. Advantageously, the operation is carried out in a fluidized bed. Preferably, the binding parameters are adjusted so that one or more of the following conditions are met:

$BV_f$ is between 80 and 150, preferably between 80 and 120;

$SV_f$ is between 5 and 40 h$^{-1}$, preferably between 8 and 20 h$^{-1}$, still more preferably between 8 and 15 h$^{-1}$;

$LV_f$ is between 3 and 4.8 m/h, preferably between 3.2 and 4 m/h.

Preferably, all of the following conditions are met during step b):

$BV_f$ is between 80 and 120;

$SV_f$ is between 8 and 15 h$^{-1}$;

$LV_f$ is between 3 and 4.8 m/h. during step c):

$BV_e$ is between 3 and 7;

$LV_e$ is less than 1 m/h.

By ion exchange, the proteins of the milk fraction used as starting material come and bind to the acid functional groups of the resin. The choice of the binding parameters according to the invention makes it possible to carry out a selective binding of the proteins onto the column. Under conventional conditions for binding milk to a cationic resin, lactoferrin and lactoperoxidase, which are predominant, preferably bind to the resin. In the process according to the invention, the other minor, proteins are favored by the binding conditions defined above and their proportion in this mixture of proteins bound to the resin is significantly greater than their proportion in the starting material. The process according to the invention thus makes it possible to isolate a milk fraction having a new protein composition relative to the prior art milk protein compositions and exhibiting advantageous biological properties.

Step c) of eluting the bound proteins is carried out under the following preferential conditions:

The resin is kept at a temperature of between 2 and 15° C., preferably between 4 and 12° C. Preferably, the column is fed with raw material (aqueous salt solution) through the top. The aqueous saline solution used for carrying out the invention is generally a solution of a chloride of an alkali metal such as K+, Na+, $Ca^{2+}$, $Mg^{2+}$. Preferably, an aqueous solution of sodium chloride is used. Advantageously, the aqueous salt solution has a concentration of between 2 and 25%, preferably of 5 to 15% by weight of salt per weight of liquid. Preferably, the ionic strength of the aqueous salt solution is between 1 and 2 M. The pH of the eluting solution is generally between 6 and 7, advantageously between 6.5 and 7.

Preferably, the elution parameters meet one or more of the following conditions:
  $BV_e$ is between 3 and 7, and preferably between 3 and 5;
  $LV_e$ is less than 0.5 m/h.

In a known manner, the column of resin is washed before another use.

After this step, the eluate obtained, containing the mixture of milk proteins, is subjected in a known manner to one or more ultrafiltration and diafiltration steps intended to remove the salts. Other means known to persons skilled in the art, such as electrodialysis or passage over weak anionic and cationic resins, can be used in this step as a replacement for ultrafiltration and diafiltration. Preferably, this treatment is carried out until a permeate having a conductivity of less than 15 mS is obtained. Any other process which makes it possible to remove the salts, such as in particular electrodialysis, can also be used in place of this step. The solution is then subjected to microfiltration intended to sterilize the ultrafiltration retentate before drying. Other technical means may be used to sterilize the milk fraction obtained in this step, in particular a suitable heat treatment, ultrasound or pulsed electric field.

Preferably, the desalted and sterilized product is dried in order to obtain the milk fraction derived from the process of the invention in the form of a powder, which then allows its packaging and its storage. In a known manner, the drying may be performed by freeze-drying or by spray-drying.

The milk protein fraction, preferably derived from cows' milk and obtained by the process according to the invention is novel. In dried form, it is characterized in that it has:
  a protein content of greater than 90%,
  a mineral salt content of less than 1%,
  a fat content of less than 1%,
  a lactose content of less than 1%,
  a moisture content of less than 5%,
  a lactoferrin content of less than 80%,
  a pH in solution at 2% of between 6 and 7.5,
  a UV-visible spectrophotometric purity defined by an $OD^{412}/OD^{280}$ ratio <0.15,
  at least 1% of proteins having an isoelectric point greater than or equal to 8, the percentages being given by weight relative to the weight of dry matter content of the milk fraction according to the invention.

In the case where the starting material used is milk and not whey, the product obtained by the process according to the invention is characterized by the additional conditions:
  presence of at least 40% of proteins having an isoelectric point greater than or equal to 8,
  the lactoferrin content is greater than 30% and less than 80%,
  the lactoperoxidase activity is greater than or equal to 120 ABTS units per mg of isolate (ABTS=2,2'-azino-bis-(3-ethyl Benzo Thiazoline 6-Sulfonic Acid).

The measurement of OD at 412 nm gives a quantitative evaluation of the lactoferrin and of lactoperoxidase present in the milk protein fraction.

The measurement of OD at 280 nm gives a quantitative evaluation of all the proteins present in the milk protein fractions.

The $OD^{412}/OD^{280}$<0.15 ratio shows that the lactoferrin and lactoperoxidase are underrepresented compared with the other proteins in the composition according to the invention in comparison with the proportions in which they are present in milk and in the milk protein fractions of the prior art.

Preferably, the milk protein fraction obtained by the process according to the invention corresponds to at least one of the following characteristics:
  a protein content of greater than 95%,
  a mineral salt content of less than 0.5%,
  a fat content of less than 0.5%,
  a lactose content of less than 0.5%,
  a moisture content of less than 4%,
  a pH in solution at 2% of between 6 and 7.2,
  a UV-visible spectrophotometric purity defined by an $OD^{412}/OD^{280}$ ratio <0.1,
  contains at least 1% of proteins having an isoelectric point of between 8.2 and 8.7.

In the case where the starting material used is milk and not whey, the product obtained by the process of the invention is characterized by the additional preferred condition:
  the lactoferrin content is greater than 50% and less than 80%.

The milk protein fractions according to the invention exhibit advantageous properties: in particular they promote the growth of osteoblast cells and that of intestinal cells.

The milk protein fractions of the invention are also effective for inhibiting the growth of osteoclasts and preosteoclasts.

These properties, and the already known properties of the milk protein fractions of the prior art make it possible to envisage the use of these compositions in numerous applications, in particular in the food and pharmaceutical sectors. The subject of the invention is therefore also any food or pharmaceutical composition and any hygiene product comprising a milk protein fraction according to the invention.

A food composition according to the invention may be for example a dietary milk, in particular a milk intended as infant food, obtained by simple rehydration of the powder of milk protein fraction according to the invention. The subject of the invention is therefore the use of a milk protein fraction according to the invention for the preparation of a dietary milk.

The subject of the invention is also food compositions comprising a milk protein fraction according to the invention and other food ingredients. It is possible in particular to envisage adding the milk protein fraction according to the invention to a cows' milk in order to enrich it in certain proteins. The presence of calcium in foods comprising the milk protein fraction according to the invention will be particularly beneficial since this milk protein fraction improves the absorption of calcium by the human body, in particular the binding of calcium in the bone tissue.

The subject of the invention is therefore also the combination of a milk protein fraction according to the invention with calcium.

The invention also relates to the dietary kits comprising several constituents packaged separately, intended for preparation of the food immediately before use and comprising powder of milk protein fraction according to the invention.

Such foods may be used for the prevention of pathologies such as: growth retardation, osteoporosis, bone fragility, bone fractures, rheumatism, osteoarthritis, periodontal diseases, intestinal barrier deficiency, and the like.

A pharmaceutical composition according to the invention, comprising at least one milk protein fraction according to the invention and a pharmaceutically acceptable carrier may be used in the treatment of one or more of the following pathologies: growth retardation, osteoporosis, bone fragility, bone fractures, rheumatism, osteoarthritis, periodontal diseases, intestinal barrier deficiency, and the like.

Of course such a composition may additionally comprise one or more other therapeutic active agents. Calcium may be advantageously combined with the milk protein fraction according to the invention. Such a combination forms part of the present invention. Indeed, a milk protein fraction according to the invention makes it possible to improve the absorption of calcium in the body, in particular the binding of calcium in the bone tissue, which makes it possible to improve the bone strengthening effect.

Calcium with vitamin D may also advantageously be combined with the milk protein fraction according to the invention. Such a combination also forms part of the present invention. Indeed, vitamin D improves the intestinal absorption of calcium and a milk protein fraction according to the invention makes it possible to improve the binding of calcium in the bone tissue. This synergistic effect makes it possible in particular to improve bone health.

Pharmaceutical compositions or dietary supplements according to the invention may be administered in any appropriate form such as in the form of a powder, granules, tablets, gelatin capsules, a drink, such as for example as a solution or as a syrup. The frequency of administration and the dose to be administered are adjusted in a known manner according to the weight and the age of the individual.

Also included in the present invention are the hygiene products, in particular the products intended for oral hygiene, such as toothpastes in gel or paste form, mouthwashes, chewing gums, comprising a milk protein fraction composition.

EXAMPLES

I—Preparation of the Milk Protein Isolates

General Conditions:

The resin used in the examples below is a Trisacryl SP® resin. It undergoes the following conditioning treatments before its initial use: bringing into contact with a 0.4% aqueous solution of the disinfectant ASEPTO®, at the rate of 3 liters of disinfectant per kilo of wet resin, followed by rinsing. Equilibration by passing an acetate buffer (80 mM, pH=5.3) containing calcium chloride (33 g/l) and potassium chloride (50 g/l), at the rate of 4 liters of this buffer per kilo of wet resin. Finally, the resin is rinsed with water until an eluate is obtained which has a pH of between 6 and 7 and a conductivity of less than 5 mS.

After each sequence of binding of raw material and elution, the resin is cleaned by enzymatic treatment with *Bacillus licheniformis* alkaline protease in buffer at pH=8, at 60° C. for 2 hours, followed by treatment with an NaCl solution at 100 g per liter for thirty minutes (repeated twice). Before its reuse it is subjected to the conditioning treatment presented above.

The ultrafiltration is carried out on the eluate at a temperature of between 5 and 10° C. on organic membranes whose cut-off is 10 kD. The volume concentration factor used is between 10 and 60, so as to obtain a retentate having the highest possible dry extract, preferably between 15 and 20%. The diafiltration is performed at a temperature of between 15 and 25° C. on the same membranes, using a volume of demineralized water of between 8 and 10 times the volume of retentate obtained at the end of the ultrafiltration until a conductivity of the permeate of less than 15 mS is obtained.

The microfiltration is carried out at 35° C. using the retentate obtained from ultrafiltration/diafiltration on ceramic membranes with a cut-off of 1.4 μm.

The microfiltration permeate is dried in a turbine spray-drying tower with an inlet temperature of 140° C. and an outlet temperature of 80° C.

Characteristic of the Resin:

The SPEC 70 resin consists of a chemically inert and mechanically resistant support.

Chemically, the support is manufactured by polymerization of AMPS: 2-acrylamide 2-methylpropanesulfonic acid. The resin has an ion-exchange capacity of between 400 and 700 μE/ml and a protein binding capacity measured on lactoferrin (minimum 20 mg/ml) or lactoperoxidase (minimum 40 mg/ml) or lysozyme (minimum 70 mg/ml); its density is greater than 1.15 and its particle size is between 250 and 560 μm.

Example 1

300 000 liters of skimmed milk, heat-treated at 68° C. for 15 seconds, are passed at 10° C. over 3000 liters of cation-exchange resin (reference SPEC 70 supplied by the company BIOSEPRA) at a flow rate of 14000 liters/h in an ascending flow in two fractionating columns in parallel and each having a radius of 1 meter.

The proteins bound to the resin are eluted with 9000 liters of a 10% sodium chloride solution in a descending flow.

The eluate obtained has a pH of 6.5 and a dry extract of 80 g/kg. It is passed over ultrafiltration membranes with a cut-off of 10 kD and having a surface area of 17 $m^2$, provided by DSS, at 11° C. with a permeation flow of 16 $l/h/m^2$ until a volume concentration factor of 7 is obtained.

The retentate has a pH of 5.9 and a dry extract of 170 g/kg; in order to remove the salt, this retentate is then diafiltered on the same membranes at 25° C. with water in an amount of 70% of the volume of eluate used and until a volume concentration factor of 9.5 is finally obtained with a permeation flow of 16 $l/h/m^2$.

The diafiltered retentate has a pH of 6.5 and a dry extract of 95 g/kg; it is then passed over microfiltration membranes having a porosity of 1.4 μm at 30° C. with a permeation flow of 320 $l/h/m^2$. The permeate of this microfiltration has a pH of 6.6 and a dry extract of 75 g/kg.

This permeate is then dried in a spray-drying tower provided with a turbine; the tower inlet temperature is 140° C. and the outlet temperature is 80° C.

The powdered isolate thus obtained has the following characteristics:
- moisture : 4.7%,
- proteins (N×6.38): 96.2% of which:
  - lactoferrin: 54%
  - lactoperoxidase: 125 ABTS unit/mg
- ash: 0.1% of which:
  - Na: 0.02%
  - Cl: 0.44%
- spectrophotometric purity: $OD^{412}/OD^{280}$=0.06.

The electrophoretic profile obtained by isoelectric focusing with silver nitrate development is illustrated by FIG. 1. In FIG. 1 are compared the distribution of the isoelectric points of the milk protein fraction according to the invention (noted LN06) and a reference product noted Std which is a protein calibration kit marketed by the company Pharmacia under the reference 17047101 and called "Isoelectric Focusing Calibration Kit Broad PI 3-10". It is observed that proteins having high isoelectric points (around 8.4) are predominantly present. This product comprises about 50% by weight of lactoferrin relative to the total weight of the isolate.

Example 2

4.4 liters of native acid serum from casein manufacture (pH 4.7, dry extract 65 g/kg) are passed at 10° C. over 22 ml of cation-exchange resin (reference SPEC 70 provided by the company BIOSEPRA) at a flow rate of 400 ml/h in descending flow in a column having a diameter of 15 mm.

The proteins bound to the resin are eluted with 90 ml of a 10% sodium chloride solution in descending flow.

In order to remove the salt, the eluate obtained (100 ml) is then dialyzed against demineralized water for 48 hours at 4° C.

The dialyzed product has the following characteristics:
dry extract: 1.5 g/kg,
pH: 5.4,
conductivity: 24 µS,
$OD^{412}<0.005$,
$OD^{280}=4.6$ (0.46 diluted 10 times).

The electrophoretic profile makes it possible to observe that at least 1% of the proteins present have an isoelectric point greater than or equal to 8. This product contains about 3% lactoferrin by weight relative to the total weight of the protein isolate.

II—Biological Tests

A—General Methods

1. Tests of Proliferation of MC3T3 Cells (Osteoblast Cell Line)

The MC3T3 cells are cultured at 37° C. in a humid atmosphere containing 5% $CO_2$. The culture medium used is α-MEM (alpha-Modified Eagle Medium) supplemented with 10% fetal calf serum and 50 U/ml of penicillin and 50 µg/ml streptomycin.

To test the effect of the various proteins on cell growth, the cells are inoculated on 48-well plates at a density of $5\times10^4$ cells/cm². 48 hours after inoculation, the proteins are added to the cells. The protein solutions are prepared in the culture medium at a concentration of 10 mg/ml and then filtered on a 0.22µ filter and diluted to the desired concentration in the culture medium immediately before use. The cells are counted after 72 h of culture by evaluating the quantity of DNA.

2. Tests of Proliferation of RAW 264.7 Cells (Preosteoclast Cell Line)

The RAW 264.7 cells are cultured at 37° C. in a humid atmosphere containing 5% of $CO_2$. The culture medium used is DMEM (Dubelcco's Modified Eagle Medium) containing 25 mM of glucose, 4 mM glutamine and 1.5 g/l of bicarbonate supplemented with 10% fetal calf serum and 50 U/ml of penicillin and 50 µg/ml streptomycin.

To test the effect of the various proteins on cell growth, the cells are inoculated on 48-well plates at a density of $5\times10^4$ cells/cm². 48 hours after inoculation, the proteins are added to the cells. The protein solutions are prepared in the culture medium at a concentration of 10 mg/ml and then filtered on a 0.22µ filter and diluted to the desired concentration in the culture medium immediately before use. The cells are counted after 72 h of culture by evaluating the quantity of DNA.

3. Test of Proliferation of Caco-2 Cells (Intestinal Cell Line

The Caco-2 cells are cultured at 37° C. in a humid atmosphere containing 5% of $CO_2$. The culture medium used is DMEM (Dubelcco's Modified Eagle Medium) containing 25 mM glucose supplemented with 15% fetal calf serum, 1% of nonessential amino acids, 6 mM glutamine and 50 U/ml of penicillin and 50 µg/ml streptomycin.

To test the effect of the various proteins on cell growth, the cells are inoculated on 48-well plates at a density of $4\times10^4$ cells/cm². 48 hours after inoculation, the proteins are added to the cells. The protein solutions are prepared in the culture medium at a concentration of 10 mg/ml and then filtered on a 0.22µ filter and diluted to the desired concentration in the culture medium immediately before use. The cells are counted after 72 h of culture by evaluating the quantity of DNA.

B—Results

The tests described above were carried out on three products:
 a cows' milk protein isolate composed of 90% lactoferrin (control product): $T_1$,
 a cows' milk protein isolate whose lactoferrin content is less than 0.01% (control product): $T_2$,
 the product prepared in example 1: $P_1$,
 the product prepared in example 2: $P_2$.

The results of these tests are presented in Table I:

TABLE I

| Product | Concentration | Stimulation of the proliferation of MC3T3 cells | Inhibition of the proliferation of RAW 264.7 cells | Stimulation of the proliferation of Caco-2 cells |
|---|---|---|---|---|
| T1 | 1.0 mg/ml | +65% | −70% | +67% |
|    | 0.1 mg/ml | +37% | −30% | +40% |
| T2 | 1.0 mg/ml | +9%  | −8%  | +9%  |
|    | 0.1 mg/ml | +6%  | −4%  | —    |
| P1 | 1.0 mg/ml | +36% | −70% | +40% |
|    | 0.1 mg/ml | +15% | −22% | +30% |
| P2 | 1.0 mg/ml | +31% | −32% | +41% |
|    | 0.1 mg/ml | +6%  | −17% | +37% |

The concentration denotes the concentration of milk protein isolates in the culture medium.

The prior art tends to demonstrate that the activity of a milk protein isolate is linked to the percentage of lactoferrin which it contains (see results of $T_2$).

Contrary to this preconception of the prior art, the results of the tests presented above show that milk protein isolates of the invention, although containing little lactoferrin compared with the control $T_1$, exhibit a remarkable activity in the tests of cell growth on osteoblasts and on intestinal cells and of inhibition of proliferation of preosteoclasts.

The invention claimed is:

1. A process for isolating milk proteins from milk or whey comprising the following steps:
   a) the milk or the whey is sterilized and defatted;
   b) the milk fraction derived from step a) is passed over a cation-exchange resin conditioned in an elution column;
   c) the fraction retained on the resin is eluted with an aqueous salt solution;

d) the eluate resulting from step c) is desalted and sterilized and wherein

α) the cation-exchange resin is a resin grafted onto strong acid functional groups;

β) during step b), the binding parameters have the following values:
BV is between 50 and 400;
SV is between 2 and 40 $h^{-1}$;
LV is greater than or equal to 1 m/h and less than or equal to 5 m/h.

γ) during step c), the elution parameters have the following values:
BV is between 1.5 and 7;
LV is less than 1 m/h.

2. The process as claimed in claim 1, wherein the starting material is cows' milk.

3. The process as claimed in claim 1, wherein the starting material is a casein acid whey.

4. The process as claimed in claim 1, wherein the cation-exchange resin is a resin grafted by acid functional groups with a pKa ≦2 having an ion-exchange capacity of between 200 and 1000 µE/ml.

5. The process as claimed in claim 4, wherein the resin is grafted by sulfonate salt or sulfonic acid functional groups.

6. The process as claimed in claim 5, wherein the resin is grafted by propyl sulfonate or propylsulfonic functional groups.

7. The process as claimed in claim 1, wherein the particle size of the resin is between 100 µm and 900 µm.

8. A process for isolating milk proteins from milk or whey comprising the following steps:

a) the milk or the whey is sterilized and defatted;
b) the milk fraction derived from step a) is passed over a cation-exchange resin conditioned in an elution column;
c) the fraction retained on the resin is eluted with an aqueous salt solution;
d) the eluate resulting from step c) is desalted and sterilized and wherein α) the cation-exchange resin is a resin grafted onto strong acid functional groups:

β) during step b), the binding parameters have the following values:
BV is between 80 and 150;
SV is between 5 and 40 $h^{-1}$;
LV is between 3 and 4.3 m/h.

γ) during step c), the elution parameters have the following values:
BV is between 1.5 and 7;
LV is less than 1 m/h.

9. A process for isolating milk proteins from milk or whey comprising the following steps:

a) the milk or the whey is sterilized and defatted;
b) the milk fraction derived from step a) is passed over a cation-exchange resin conditioned in an elution column;
c) the fraction retained on the resin is eluted with an aqueous salt solution;
d) the eluate resulting from step c) is desalted and sterilized and wherein α) the cation-exchange resin is a resin grafted onto strong acid functional groups:

β) during step b), the binding parameters have the following values:
BV is between 80 and 120;
SV is between 8 and 15 $h^{-1}$;
LV is between 3 and 4.8 m/h. during step c):

BV is between 3 and 7;
LV is less than 1 m/h.

10. The process as claimed in claim 1, wherein during step b), the resin is conditioned in a column whose temperature is kept between 2 and 15° C.

11. A process for isolating milk proteins from milk or whey comprising the following steps:

a) the milk or the whey is sterilized and defatted;
b) the milk fraction derived from step a) is passed over a cation-exchange resin conditioned in an elution column;
c) the fraction retained on the resin is eluted with an aqueous salt solution;
d) the eluate resulting from step c) is desalted and sterilized and wherein α) the cation-exchange resin is a resin grafted onto strong acid functional groups;

β) during step b), the binding parameters have the following values:
BV is between 50 and 400;
SV is between 2 and 40 $h^{-1}$;
LV is greater than or equal to 1 m/h and less than or equal to 5 m/h. wherein during step c) for elution of the bound proteins, at least one of the following conditions is met:
BV is between 3 and 5;
LV is less than 0.5 m/h.

12. The process as claimed in claim 1, wherein during step c), the resin is conditioned in a column whose temperature is kept between 2 and 15° C.

13. The process as claimed in claim 1, wherein the aqueous salt solution used for carrying out the invention is a solution of a chloride of an alkali metal chosen from $K^+$, $Na^+$, $Ca^{2+}$, $Mg_{2+}$.

14. The process as claimed in claim 12, wherein the aqueous salt solution is an aqueous sodium chloride solution.

15. The process as claimed in claim 14, wherein the aqueous salt solution has a concentration of between 2 and 25% by weight of salt per weight of liquid.

16. The process as claimed in claim 14, wherein the aqueous salt solution has an ionic strength of between 1 and 2 M.

17. The process as claimed in claim 1, wherein the pH of the aqueous salt solution for elution is between 6 and 7.

18. The process as claimed in claim 1, wherein the desalting is carried out by ultrafiltration and diafiltration.

19. The process as claimed in claim 18, wherein the ultrafiltration and diafiltration treatments are carried out until a permeate having a conductivity of less than 15 mS is obtained.

20. The process as claimed in claim 1, wherein the sterilization is carried out by microfiltration.

21. The process as claimed in claim 1, wherein the desalted and sterilized product is dried so as to obtain the milk fraction derived from the process of the invention in the form of a powder.

22. A milk protein fraction obtained by the process according to claim 1.

23. The milk protein fraction as claimed in claim 22 which is derived from a casein acid whey.

24. A combination of a milk protein fraction according to claim 22 with calcium.

25. The combination as claimed in claim 24, additionally including vitamin D.

26. A food composition, comprising a milk protein fraction according to claim 22.

27. A dietary kit comprising a milk protein fraction as claimed in claim 22 wherein said milk protein fraction is a powder.

28. A dietary milk prepared from a milk protein fraction as claimed in claim 22.

29. A food intended for the treatment of a pathology selected from: growth retardation, osteoporosis, bone fragility, bone fractures, rheumatism, osteoarthritis, periodontal diseases, and intestinal barrier deficiency, or intended to promote the growth of osteoblasts and/or of intestinal cells and/or to inhibit the growth of preosteoclasts, said food being prepared from a milk protein fraction as claimed in claim 22.

30. A pharmaceutical composition, comprising at least one milk protein fraction as claimed in claim 22 and a pharmaceutically acceptable edible carrier.

31. A medicament intended for the treatment of a pathology selected from: growth retardation, osteoporosis, bone fragility, bone fractures, rheumatism, osteoarthritis, periodontal diseases, and intestinal barrier deficiency, or intended to promote the growth of obsteoblasts and/or of intestinal cells and/or to inhabit the growth of preosteoclasts, said medicament comprising a milk protein fraction as claimed in claim 22.

32. A method for preparing a medicament intended to improve the absorption of calcium in the body of an individual, wherein said method includes the step of introducing a milk protein fraction as claimed in claim 22, into said medicament.

33. A hygiene product comprising at least one milk protein fraction as claimed in claim 22.

\* \* \* \* \*